(12) United States Patent
Kodama et al.

(10) Patent No.: US 9,017,257 B2
(45) Date of Patent: Apr. 28, 2015

(54) ACTIVITY MONITOR, METHOD OF CALCULATING TARGET ACTIVITY AMOUNT, AND STORAGE MEDIUM

(75) Inventors: Miyuki Kodama, Itabashi-Ku (JP); Jun Kato, Itabashi-Ku (JP); Mayumi Yamashita, Itabashi-Ku (JP); Shizuka Takahashi, Itabashi-Ku (JP)

(73) Assignee: Tanita Corporation, Tokyo (JP)

( * ) Notice: Subject to any disclaimer, the term of this patent is extended or adjusted under 35 U.S.C. 154(b) by 375 days.

(21) Appl. No.: 13/308,978

(22) Filed: Dec. 1, 2011

(65) Prior Publication Data

US 2012/0209533 A1 Aug. 16, 2012

(30) Foreign Application Priority Data

Feb. 16, 2011 (JP) ................................. 2011-031323

(51) Int. Cl.
*G06F 19/00* (2011.01)
*A61B 5/11* (2006.01)
*A61B 5/00* (2006.01)

(52) U.S. Cl.
CPC ............. *A61B 5/1118* (2013.01); *A61B 5/4866* (2013.01); *G06F 19/3481* (2013.01); *G06F 19/3475* (2013.01)

(58) Field of Classification Search
CPC ............ A61B 5/00; A61B 5/05; A61B 10/10; G06Q 10/00; G09B 19/00
USPC ................ 600/300, 547, 551; 705/2; 434/127
See application file for complete search history.

(56) References Cited

U.S. PATENT DOCUMENTS

| | | | | |
|---|---|---|---|---|
| 5,839,901 A * | 11/1998 | Karkanen | | 434/127 |
| 6,402,699 B1 * | 6/2002 | Kodama et al. | | 600/551 |
| 6,605,038 B1 * | 8/2003 | Teller et al. | | 600/300 |
| 6,665,561 B2 * | 12/2003 | Baba et al. | | 600/547 |
| 6,694,182 B1 | 2/2004 | Yamazaki et al. | | |
| 7,008,350 B1 | 3/2006 | Yamazaki et al. | | |
| 7,361,141 B2 * | 4/2008 | Nissila et al. | | 600/300 |

(Continued)

FOREIGN PATENT DOCUMENTS

JP 2005-058614 A 3/2005
JP 2007-505412 A 3/2007

(Continued)

OTHER PUBLICATIONS

Partial European Search Report issued May 15, 2012, in the corresponding European Application No. 12000809.9-1526. (6 pages).
Japanese Office Action dated Apr. 25, 2014, issued by the Japanese Patent Office in corresponding Japanese Patent Application No. 2013-110824 (2 pages).

*Primary Examiner* — William Thomson
*Assistant Examiner* — Victor Shapiro
(74) *Attorney, Agent, or Firm* — Buchanan, Ingersoll & Rooney PC

(57) ABSTRACT

The activity monitor (100) includes a basic information acquisition unit (20) that accepts input of basic physical information (BA) of the user's body, a target information acquisition unit (30) that accepts input of the user's target physical expenditure (CS), an activity pattern acquisition unit (40) that acquires pattern information indicating the user's intent on the activity amount (AM), and a target activity calculation unit (50) that determines a target activity amount (TA) on the basis of the basic physical information (BA), the target physical expenditure (CS), and the pattern information acquired by the activity pattern acquisition unit (40).

16 Claims, 7 Drawing Sheets

(56) References Cited

U.S. PATENT DOCUMENTS

| | | | |
|---|---|---|---|
| 8,073,707 B2 * | 12/2011 | Teller et al. | 705/2 |
| 8,398,546 B2 | 3/2013 | Pacione et al. | |
| 2002/0019585 A1 | 2/2002 | Dickinson | |
| 2002/0099274 A1 * | 7/2002 | Isomura et al. | 600/300 |
| 2005/0113650 A1 | 5/2005 | Pacione et al. | |

FOREIGN PATENT DOCUMENTS

| JP | 2008-246175 A | 10/2008 |
|---|---|---|
| JP | 2008-250967 A | 10/2008 |

* cited by examiner

ACTIVITY MONITOR, METHOD OF CALCULATING TARGET ACTIVITY AMOUNT, AND STORAGE MEDIUM

This application is based on Japanese patent application NO. 2011-031323, the content of which is incorporated hereinto by reference.

BACKGROUND

1. Technical Field

The present invention relates to an activity monitor, a method of calculating a target activity amount, and a storage medium in which a program for the activity monitor is stored.

2. Related Art

Total energy expenditure of a human can be broadly classified into basal metabolism and energy expenditure through physical activities. In addition, it is known that meal-induced thermogenesis, which is an increase in body temperature that takes place after a meal, also consumes energy. When the total energy expenditure exceeds energy intake, primarily fat is burnt and body weight is reduced. Thus far, various activity monitors that measure the total energy expenditure have been developed.

For example, JP-A No. 2005-58614 discloses an activity monitor for women that calculates the total energy expenditure taking into account variations in physiological condition of women. The activity monitor estimates the physiological condition of a user on the basis of information indicating the number of elapsed days from the first day of a menstrual period, to thereby accurately calculate the user's basal metabolism and energy expenditure by exercise. The activity monitor first calculates a target fat-burning energy per day by dividing a target amount of fat loss by a target period of the diet, and outputs a target number of steps converted from the target fat-burning energy. In this calculation, the activity monitor takes into account the fact that the basal metabolism and exercise efficiency of women vary between a luteal phase and a follicular phase in a menstrual cycle. More specifically, the activity monitor decides whether the female user is in the luteal phase or the follicular phase, and applies a correction coefficient statistically determined in advance to thereby calculate the target number of steps corresponding to the target fat-burning energy per day, with respect to each phase of the menstrual cycle.

[Patent Document 1] Japanese Laid-open patent publication No. 2005-58614

To calculate the target number of steps corresponding to the target fat-burning energy per day during the luteal phase and the follicular phase with the activity monitor according to Patent Document 1, a luteal phase correction coefficient and a follicular phase correction coefficient, respectively determined statistically in advance, are employed. Since these correction coefficients are statistic values obtained on the basis of physical features, the same correction coefficients are applied to a plurality of users having common basic physical data such as age, sex, and weight. Accordingly, the same target number of steps is proposed in common to different users having the same basic physical data, provided that the users are aiming at the same diet goal (for example, losing 3 kgs. in three months).

However, although the basic physical data of the users is the same, some users wish to reduce fat primarily by limiting energy intake (amount of meal), so-called an eat less/move less type, while some users wish to actively perform exercises without limiting the energy intake, an eat more/move more type. This is the case with both male and female users. In the case of women, some users actively perform exercises even during the menstrual period, while some choose to refrain from exercising during the menstrual period. Thus, specific activity patterns for the diet largely vary depending on the users. The activity monitor according to Patent Document 1, therefore, still has a room for improvement from the viewpoint of offering meticulous options of the target number of steps so as to fit the activity patterns that are different by users irrespective of sex.

SUMMARY

The present invention has been accomplished in view of the foregoing situation, and provides an activity monitor and a method of calculating a target activity amount capable of presenting a target activity amount in meticulously prepared patterns that fit the desire of individual users.

In one embodiment, there is provided an activity monitor having an activity amount measurement unit that measures an activity amount of a user, including a basic information acquisition unit that accepts an input of basic physical information on the user's body, a target information acquisition unit that accepts an input of a target physical expenditure of the user, an activity pattern acquisition unit that acquires pattern information indicating the user's intent on the activity amount, and a target activity calculation unit that determines a target activity amount on the basis of the basic physical information, the target physical expenditure, and the pattern information acquired by the activity pattern acquisition unit.

In another embodiment, there is provided a method of calculating a target activity amount, including accepting an input of basic physical information on a user's body, accepting an input of a target physical expenditure of the user, acquiring pattern information indicating the user's intent on the activity amount, and determining the target activity amount on the basis of the basic physical information, the target physical expenditure, and the pattern information.

With the foregoing activity monitor and calculation method, the target activity amount is determined on the basis of the pattern information indicating the user's intent on the activity amount. Such an arrangement allows the target activity amount to be meticulously determined so as to fit the individual user's activity pattern, despite that a plurality of users bearing the same basic physical information inputs the same target physical expenditure.

It is to be noted that the constituents of the present invention do not necessarily have to be individually independent, but may be configured such that a plurality of constituents constitutes a single member, that a constituent is composed of a plurality of members, that a constituent is a part of another constituent, that a part of a constituent and a part of another constituent overlap, and so forth.

Although a plurality of steps is sequentially stated, such sequence in no way limits the order or timing for practically performing those steps, unless so expressed, for executing the target activity amount calculation method according to the present invention. The order of the plurality of steps may be modified unless inconvenience is incurred in the manufacturing process, and the execution timing of one of the steps may partially or entirely overlap that of another.

The activity monitor and the calculation method according to the present invention allow the target activity amount to be presented in meticulously prepared patterns that fit the desire of individual users.

BRIEF DESCRIPTION OF THE DRAWINGS

The above and other objects, advantages and features of the present invention will be more apparent from the following description of certain preferred embodiments taken in conjunction with the accompanying drawings, in which.

DETAILED DESCRIPTION

Figure 1:
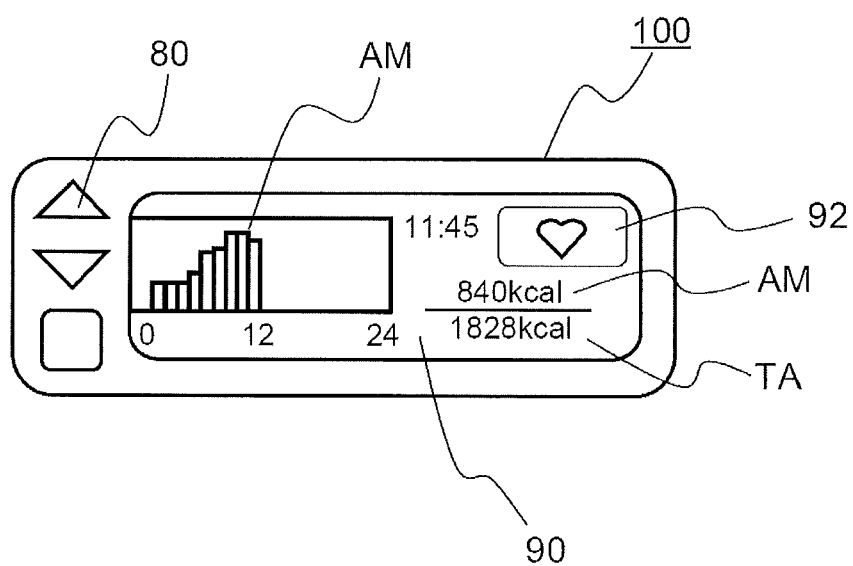
FIG. 1 is a schematic front view of an activity monitor according to a first embodiment of the present invention.

The invention will be now described herein with reference to illustrative embodiments. Those skilled in the art will recognize that many alternative embodiments can be accomplished using the teachings of the present invention and that the invention is not limited to the embodiments illustrated for explanatory purposes.

Hereafter, embodiments of the present invention will be described referring to the drawings. In all the drawings, the same constituents will be given the same numeral and the description thereof will not be repeated.

First Embodiment

FIG. 1 is a schematic drawing showing an appearance of an activity monitor 100 according to a first embodiment. The activity monitor 100 includes an input unit 80 having an operation button with which a user performs an input, and an output unit 90 that displays and outputs a measurement result of an activity amount AM and other information. Alternatively, the output unit 90 may be set up as a touch panel in which the operation button of the input unit 80 is incorporated.

The activity monitor 100 has a flexible structure, and the user attaches the activity monitor 100 to the clothes or the like during his/her daily life. The activity monitor 100 includes an acceleration sensor (not shown), to measure the user's energy expenditure by exercise such as walking or running. The activity monitor 100 also calculates the basal metabolism of the user on the basis of the user's age, sex and weight inputted through the input unit 80. Accordingly, the activity monitor 100 can calculate the user's total energy expenditure. Therefore, the activity monitor 100 can calculate the energy expenditure corresponding to the basal metabolism as the activity amount AM and display that value on the output unit 90, even though the user wearing the activity monitor 100 has not made any exercise all day long. The output unit 90 may display the energy expenditure by exercise instead of or together with the activity amount AM. Alternatively, the output unit 90 may be set to alternately display the activity amount AM and the energy expenditure by exercise, through operation of the input unit 80. The output unit 90 may also display the target activity amount of the day TA. Such an arrangement allows the user to visually recognize how much exercise has to be made in order to achieve the target of the day.

In this embodiment, the activity amount is synonymous with the total energy expenditure. When the user's body weight is stable, the total energy expenditure and the energy intake are equilibrated.

Figure 2:
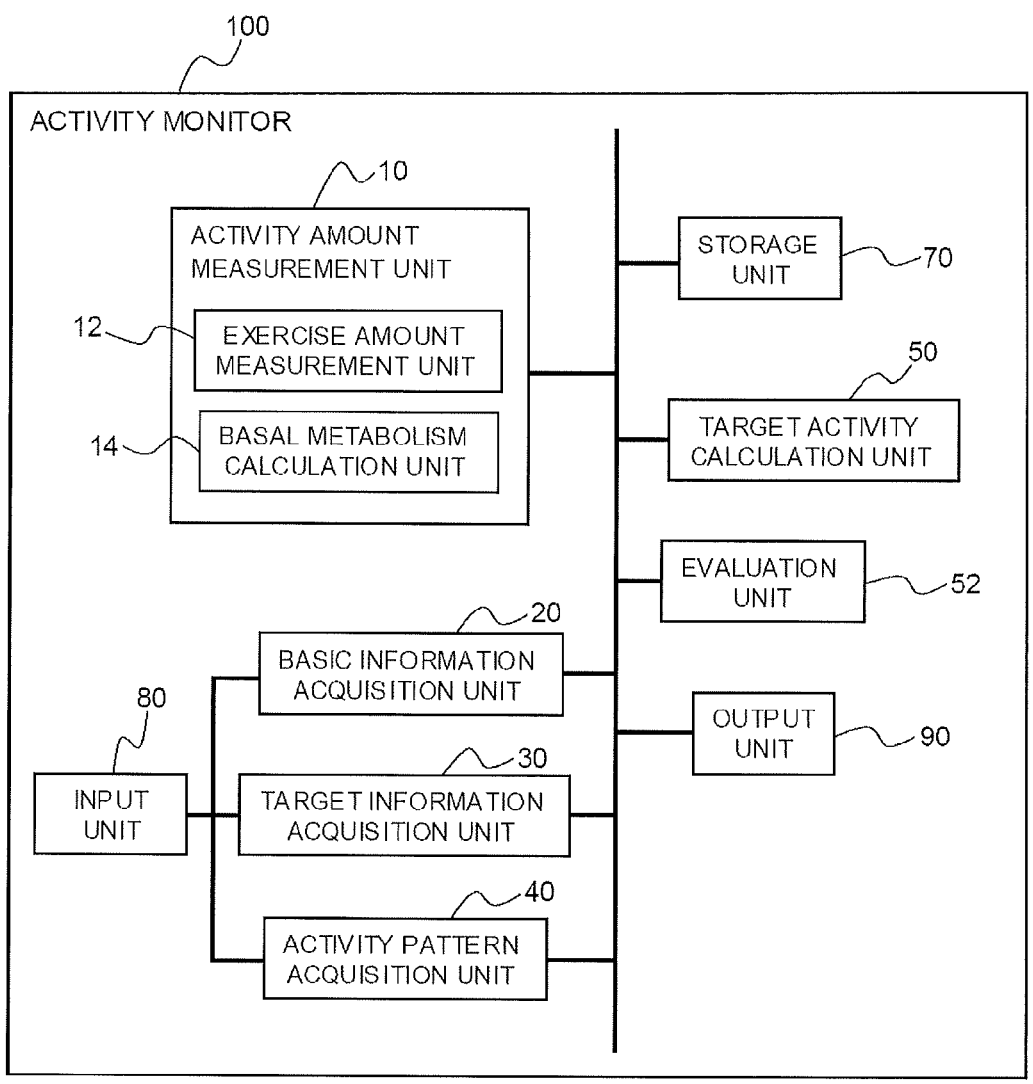
FIG. 2 is a functional block diagram of the activity monitor according to the first embodiment.

A general configuration of the monitor 100 according to this embodiment will be described. FIG. 2 is a functional block diagram of the activity monitor 100.

The activity monitor 100 includes an activity amount measurement unit 10 that measures the user's activity amount AM. The activity monitor 100 includes a basic information acquisition unit 20 that accepts an input of basic physical information BA on the user's body, a target information acquisition unit 30 that accepts an input of a target physical expenditure CS of the user, an activity pattern acquisition unit 40 that acquires pattern information indicating the user's intent on the activity amount AM, and a target activity calculation unit 50 that determines a target activity amount TA on the basis of the basic physical information BA, the target physical expenditure CS, and the pattern information acquired by the activity pattern acquisition unit 40.

Each constituent of the present invention has only to be capable of performing its function, and may be constituted in a form of, for example, an exclusive hardware that performs a predetermined function, a data processor in which a predetermined function is incorporated as a computer program, a predetermined function realized in a data processor by a computer program, and an optional combination thereof. Also, the activity monitor according to the present invention may be embodied in a form of a hardware constructed of general-purpose devices such as a central processing unit (CPU), a read-only memory (ROM), a random access memory (RAM), and an interface (I/F) unit, exclusive logic circuits designed to execute predetermined data processing, and an appropriate combination thereof, so as to read out a computer program and thereby execute the corresponding data processing.

Figure 3:
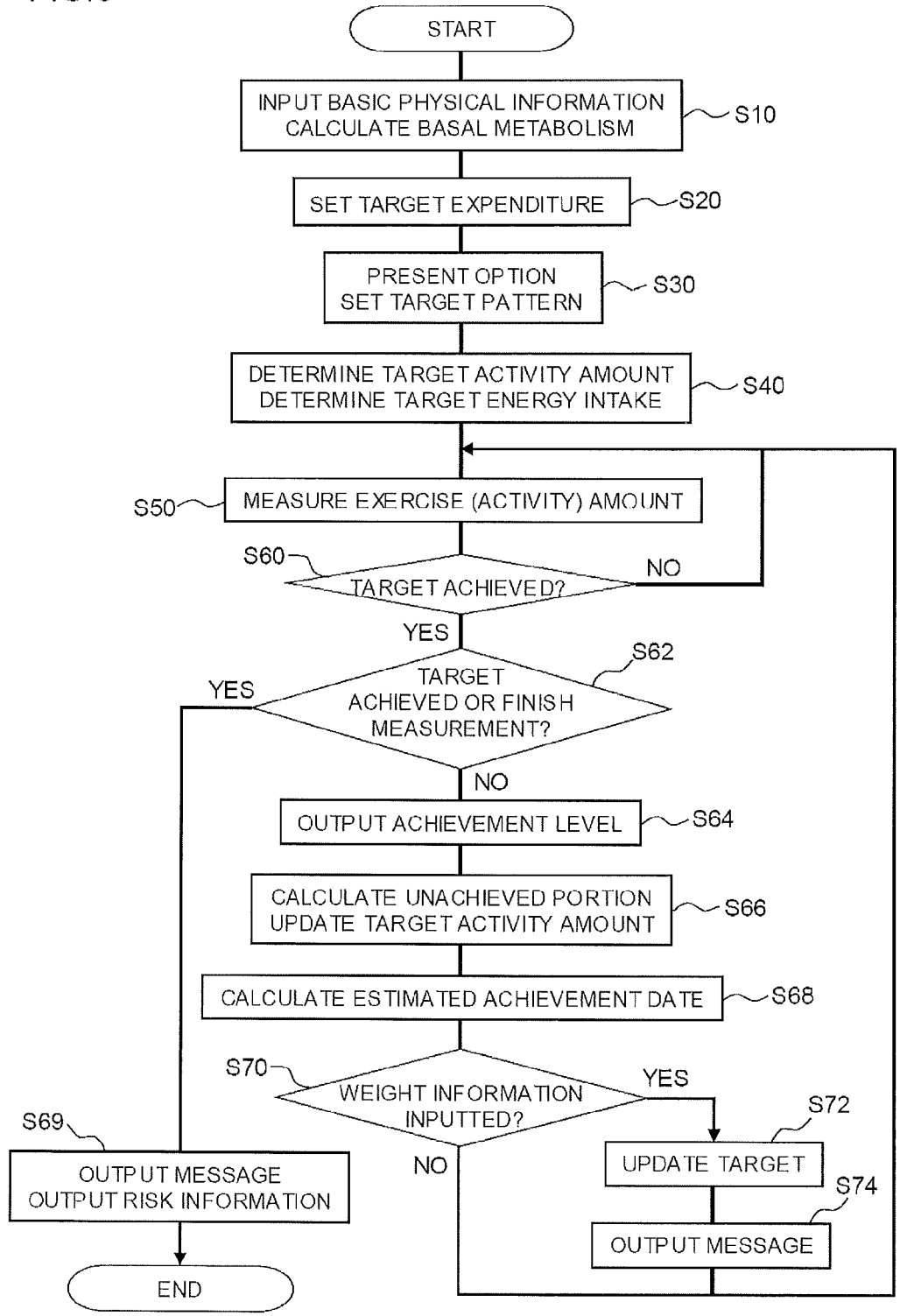
FIG. 3 is a flowchart showing a target activity amount calculation process according to the first embodiment.

A method of calculating the target activity amount (hereinafter, simply calculation method as the case may be) to be performed by the activity monitor 100 according to this embodiment will now be described in details. FIG. 3 is a flowchart showing the calculation process.

The method of calculating the target activity amount according to this embodiment includes inputting the basic physical information (step S10), setting a target expenditure (step S20), setting a target pattern (step S30), and determining the target (step S40).

In the step S10 of inputting the basic physical information, the basic information acquisition unit 20 accepts an input of the basic physical information BA regarding the user's body. In the step S20 of setting the target expenditure, the target information acquisition unit 30 accepts an input of the user's target physical expenditure CS. In the step S30 of setting the target pattern, the activity pattern acquisition unit 40 acquires the pattern information indicating the user's intent on the activity amount AM. In the target decision step S40, the target activity calculation unit 50 determines the target activity amount TA on the basis of the basic physical information BA, the target physical expenditure CS, and the pattern information.

A program according to this embodiment causes the activity monitor 100 incorporated with the activity amount measurement unit 10 to execute the calculation of the target activity amount. The calculation process of the target activity amount includes, as stated above, accepting the input of the basic physical information BA regarding the user's body, accepting the input of the user's target physical expenditure CS, acquiring the pattern information indicating the user's intent on the activity amount AM, and determining the target activity amount TA on the basis of the basic physical information BA, the target physical expenditure CS, and the pattern information. A storage medium according to this embodiment contains such a program.

The activity monitor 100 is an apparatus that measures the user's activity amount AM and aggregates the activity amounts by a predetermined period. The period is typically set as one day, however the activity amounts AM may be aggregated through a week. The activity amount AM herein means total energy expenditure, which is the total of energy expenditure by exercise, basal metabolism, and meal-induced thermogenesis. The basal metabolism may be statistically obtained on the basis of the age, sex, and weight of the user. The meal-induced thermogenesis varies in proportion to energy intake, and generally approximately one sixth of the basal metabolism. In this embodiment, information including at least the user's age, sex, and weight is acquired as the basic physical information BA.

The basic information acquisition unit 20 acquires such basic physical information BA inputted through the input unit 80, and stores the basic physical information BA in the storage unit 70. The storage unit 70 contains a table or a function (metabolism calculation information) indicating relationships between the age, sex, and weight and the basal metabolism. In this embodiment, the metabolism calculation information is a table or a function containing the equation (1) cited below and a reference basal metabolism.

[Equation 1]

$$\text{Basal metabolism(kcal/day)} = \text{reference basal metabolism(kcal/kg/day)} \times \text{user's body weight(kg)} \quad (1)$$

The reference basal metabolism represents standard basal metabolism of a human by age group and sex. The reference basal metabolism is expressed as basal metabolism per day and per kg of body weight. For example, the reference basal metabolism of Japanese women of 30 to 49 years old is 21.7 kcal/kg/day, and that of Japanese men of the same age group is 22.3 kcal/kg/day. The equation (1) cited above and such values of the reference basal metabolism appear in "Dietary Reference Intake of Japanese People" published by the Ministry of Health, Labor and Welfare of Japan.

It is preferable to store in the storage unit 70 the data of reference basal metabolism of people in the countries or regions where the activity monitor 100 is to be used.

According to this embodiment, for example, the basal metabolism of a woman having an initial weight of 50 kgs. can be calculated as 1085 kcal/day, on the basis of the above cited reference basal metabolism and the equation (1).

The activity amount measurement unit 10 includes an exercise amount measurement unit 12 that measures the user's exercise amount (energy expenditure by exercise) and a basal metabolism calculation unit 14 that calculates the user's basal metabolism on the basis of the basic physical information BA. The exercise amount measurement unit 12 includes an acceleration sensor (not shown) and an arithmetic unit (not shown) that performs a predetermined calculation on the acceleration data outputted by the acceleration sensor, to thereby calculate the user's energy expenditure by exercise. The basal metabolism calculation unit 14 calculates the user's basal metabolism on the basis of the basic physical information BA and the metabolism calculation information stored in the storage unit 70 (step S10 in FIG. 3).

Hereafter in this embodiment, the user will be exemplified by a woman in the thirties having a body weight of 50 kgs. at the time of starting the diet.

The target information acquisition unit 30 acquires the target physical expenditure CS inputted through the input unit 80 and stores the target physical expenditure CS in the storage unit 70 (step S20). An item that can be converted into a loss of the user's body weight may be adopted as the target physical expenditure CS. Alternatively, an item that can be converted into a weight loss ratio, loss of body fat amount, percentage of body fat loss, loss of BMI, and so forth. In addition, a period for the diet may be acquired from the user as the target physical expenditure CS, or a predetermined period (for example, three months or six months) programmed in advance may be employed to determine the target activity amount TA.

In this embodiment, it will be assumed that the target of the diet is losing 3 kgs. in three months (=90 days).

Now, it is known that the basal metabolism is directly proportional to the body weight. Accordingly, the basal metabolism calculated on the basis of the user's weight at the time of starting the diet (initial weight) is greater than the user's basal metabolism at the time that the target of the diet is achieved. Therefore the basal metabolism calculated on the basis of the user's initial weight is estimated to be greater than the basal metabolism at the time of achievement of the diet target. In other words, the basal metabolism gradually decreases with the progress of the diet. Accordingly, the target activity amount TA has to be gradually reduced with the progress of the diet, otherwise excessive energy expenditure by exercise would be required in an ending period of the diet, which imposes a heavy burden on the user. In other words, the diet target may gradually shift toward the eat more/move more type away from the activity pattern desired by the user, unless the target activity amount TA is gradually reduced through the diet period. To avoid such a disadvantage, the basal metabolism calculation unit 14 according to this embodiment may calculate the basal metabolism on the basis of an intermediate body weight between the initial weight and the weight at the time of achievement of the diet target. The weight at the time of achievement of the diet target can be obtained on the basis of the user's initial weight and the target physical expenditure CS.

The meal-induced thermogenesis will now be described hereunder. The meal-induced thermogenesis is directly proportional to energy intake. As will be subsequently described, tracking weight information indicating the transition of the user's body weight allows the user's energy intake to be estimated. Accordingly, the meal-induced thermogenesis that fluctuates with the progress of the diet can be calculated. Also, it is preferable to perform preliminary measurement of the user's activity amount at the time of starting the diet, as will be described in a second embodiment. At the time of starting the diet, normally the user's body weight can be presumed to be stable and hence the user's energy intake and the total energy expenditure are equilibrated. The total energy expenditure is the total of the activity amount and the meal-induced thermogenesis. The correlation between the meal-induced thermogenesis and the energy intake can be statistically obtained. Accordingly, performing the preliminary measurement of the user's activity amount allows the user's meal-induced thermogenesis and energy intake at the time of starting the diet to be calculated.

In this embodiment, however, the meal-induced thermogenesis is not taken into account for the sake of clarity of the description, and the user's total energy expenditure will be calculated on the basis of the following equation (2) and a physical activity level (PAL) cited in "Dietary Reference Intake of Japanese People".

[Equation 2]

$$\text{Total energy expenditure(kcal/day)} = \text{estimated energy requirement(kcal/day)} = \text{basal metabolism(kcal/day)} \times \text{physical activity level(PAL)} \quad (2)$$

The physical activity level (PAL) is an index obtained by dividing a total energy expenditure measured by a doubly labeled water method by the basal metabolism, and classified into a level I to a level III. The level I designates a low level, and the representative value of the physical activity level is 1.50. The level II designates an ordinary level, and the representative value of the physical activity level is 1.75. The level III designates a high level, and the representative value of the physical activity level is 2.00. These representative values of the physical activity level are stored in the storage unit 70.

In this embodiment, the total energy expenditure can be calculated as 1899 (=1085×1.75) (kcal/day) on the basis of the equation (2) and the physical activity level (for example, level II=1.75). This indicates a standard condition in which the user's body weight before the diet is stabilized without significant fluctuation and the energy intake and the total energy expenditure (activity amount) are equilibrated. Hereinafter, the total energy expenditure may be referred to as standard activity amount, as the case may be.

The activity pattern acquisition unit 40 accepts an input of the pattern information by the user, so as to acquire the pattern information indicating the individual user's intent on the activity amount AM. The pattern information represents the activity pattern that the user desires to carry out the diet, which can be exemplified by many types of information. In this embodiment, a physical activity level and a distribution ratio will be adopted as the pattern information. Alternatively, the pattern information may be acquired by indicating to present some target variation patterns TP to the user and accepting an input of the selected one, as will be described in the second embodiment.

The activity pattern acquisition unit 40 according to this embodiment accepts the input of the physical activity levels I to III. More specifically, the activity monitor 100 displays a questionnaire (option) of the user's physical activity level on the output unit 90, and accepts the input by the user through the input unit 80 (step S30 in FIG. 3). Thus, the activity pattern acquisition unit 40 acquires the information inputted through the input unit 80.

The activity pattern acquisition unit 40 also accepts the input of the distribution ratio through the input unit 80. The distribution ratio is a ratio of a decrease in energy intake to an increase in energy expenditure by exercise. In other words, the distribution ratio is an index that indicates a balance between restriction of energy intake and fat expenditure by exercise for achieving the diet target (target physical expenditure CS), or other values that can be converted into such an index.

The distribution ratio may be specifically determined in various manners. In this embodiment, for example, the distribution ratio is set so as to achieve 70% of the target physical expenditure CS by restricting the energy intake, and 30% thereof by burning fat by exercise.

Alternatively, a target energy decrease from the energy intake before the diet (for example, 200 kcal/day) may be adopted as the distribution ratio. Otherwise, a target energy increase from the energy expenditure by exercise before the diet (for example, 100 kcal/day) may be adopted as the distribution ratio. In this case, it suffices that one the target decrease in energy intake or the target increase in energy expenditure by exercise is inputted, because the other target value can be calculated from the difference between the target physical expenditure CS and the inputted target value.

Thus, the activity pattern acquisition unit 40 according to this embodiment acquires the information indicating the distribution ratio of the decrease in energy intake to the increase in energy expenditure by exercise, as the pattern information.

The target activity calculation unit 50 determines the target energy intake TC and the target activity amount TA on the basis of such distribution information and the target physical expenditure CS (step S40).

Such an arrangement allows the target energy intake TC and the target activity amount TA to be set in an optimum balance in accordance with the user's activity pattern such as the eat less/move less type and the eat more/move more type. In addition, performing the preliminary measurement of the user's activity amount AM thereby acquiring the pattern information as in this embodiment, on the premise that the energy intake and the total energy expenditure of the user are equilibrated, enables the user's energy intake before the diet to be estimated. Taking the distribution ratio into account in addition to the pattern information as in this embodiment allows a moderate diet target that fits the user's energy intake.

The target activity calculation unit 50 determines the target activity amount TA on the basis of the basic physical information BA, the target physical expenditure CS, and the pattern information acquired by the activity pattern acquisition unit 40. The target activity amount TA is the target of the total energy expenditure (kcal/day). The target activity calculation unit 50 according to this embodiment may also calculate the target energy intake TC and the energy expenditure by exercise (or a value converted into the number of walking steps) in addition to the target activity amount TA, and display those values on the output unit 90.

The target activity calculation unit 50 calculates the target activity amount TA as follows. Since the target physical expenditure CS is set as burning 3 kgs. of fat in three months (=90 days) in this embodiment, the amount of fat to be burnt per day can be calculated as the following equation (3).

[Equation 3]

$$\text{Target fat loss } Z \text{ per day(kcal/day)} = 3 \text{ kg}/90 \text{ days} \times 7200(\text{kcal/kg}) = 240(\text{kcal/day}) \quad (3)$$

Further, the distribution ratio according to this embodiment is set as 7:3, 7 representing the decrease in energy intake and 3 representing the increase in energy expenditure by exercise. Accordingly, the target decrease in energy intake can be set as reducing 168 kcal/day (Z×0.7) from the energy intake before the diet. Likewise, the target increase in energy expenditure by exercise can be set as increasing 72 kcal/day (Z×0.3) from the exercise amount before the diet.

In this embodiment, therefore, the target activity amount TA and the target energy intake TC can be calculated as the following equations (4) and (5) (step S40).

[Equation 4]

$$\text{Target activity amount } TA = \text{standard activity amount} + \text{increase in energy expenditure by exercise} = 1899 + 72(\text{kcal/day}) = 1971(\text{kcal/day}) \quad (4)$$

[Equation 5]

$$\text{Target energy intake } TC = \text{standard activity amount} - \text{decrease in energy intake} = 1899 - 168(\text{kcal/day}) = 1731(\text{kcal/day}) \quad (5)$$

The target activity amount TA and the target energy intake TC are displayed on the output unit 90. The user can visually confirm the displayed values to thereby plan the exercise and restriction of the meal for the day. The activity amount AM and the exercise amount of the user during the diet thus planned are measured by the activity amount measurement unit 10 (step S50). This measurement is continuously performed until an achievement level evaluation, programmed to be performed at predetermined intervals, is made (NO at step S60).

The evaluation unit 52 compares the target activity amount TA calculated as above and the activity amount AM measured by the activity amount measurement unit 10, to thereby evaluate the achievement level AC.

The evaluation unit 52 measures the user's activity amount AM, and evaluates the achievement level AC with respect to the target activity amount TA at predetermined intervals (YES at step S60). In this embodiment, the interval is set as one day. Alternatively, the interval of evaluation may be selected by the user so as to collectively evaluate the achievement level AC, for example, week by week.

More specifically, the achievement level evaluation according to this embodiment includes evaluating a difference between an activity amount expended, which is the total of the daily exercise amount (energy expenditure by exercise) actually measured by the exercise amount measurement unit 12 and the basal metabolism, and the target activity amount TA. The achievement level AC refers to such a difference. Alternatively, the achievement level AC may be determined by dividing the activity amount expended by the target activity amount TA. Further, without limitation to this embodiment, the achievement level AC may be determined by dividing the daily exercise amount actually measured by the exercise amount measurement unit 12 by the target energy expenditure by exercise, which is obtained by subtracting the basal metabolism from the target activity amount TA. In the case where the measurement is decided to be finished because a cumulative amount of fat loss Z after starting the diet has reached the target physical expenditure CS, or because the diet period is through (YES at step S62), the process advances to the step S69, and otherwise (NO at step S62) the process is successively performed.

The evaluation result of the achievement level AC is displayed on the output unit 90. In view of this, the user can plan the pace distribution for the rest of the diet period, so as to achieve the target physical expenditure CS. In the case where the achievement level AC is zero or a positive value, the activity monitor 100 displays the achievement level and a message indicating that the diet target for the day has been achieved, on the output unit 90 (step S64). In the case where the achievement level AC is a negative value, the activity monitor 100 displays the achievement level and a message indicating that the diet target for the day has not been achieved, on the output unit 90 (step S64).

The target activity calculation unit 50 calculates an unachieved portion TR of the target physical expenditure CS on the basis of the cumulative amount of the activity amount AM measured by the activity amount measurement unit 10, and updates the target activity amount TA in accordance with the unachieved portion TR (step S66). The cumulative amount of the activity amount AM is obtained from the sum of the activity amounts AM measured after starting the diet. More specifically, the unachieved portion TR is obtained by subtracting a total fat burning energy, which is a cumulative sum of the differences between the activity amount Am and the standard activity amount per day, from the target physical expenditure CS (value converted into fat burning energy). The target activity calculation unit 50 updates the target activity amount TA and the target energy intake TC such that the unachieved portion TR is evenly achieved during the rest of the diet period.

According to this embodiment, in the case where, upon comparison of the planned target activity amount TA and the actual activity amount AM, the energy expenditure is performed so as to exceed the target, the target activity amount TA for the subsequent period can be updated to a value lower than the initial setting. Conversely, in the case where the initial target activity amount TA has not been achieved, the value corresponding to the unachieved portion can be added so as to update the target activity amount TA to a value greater than the initial setting. Such an arrangement allows the user to be effectively led to the achievement of the target physical expenditure CS initially set by the user. In addition, the user is positively encouraged to expend the energy in a pace exceeding the target activity amount TA. In particular, since the user is highly willing to carry out the diet in the preliminary measurement period, an activity amount greater than the user's usual activity amount before the diet may be measured as the activity amount AM and reflected in the preliminary measurement result AM0. Accordingly the target activity amount TA is set at a relatively higher level, because of which the user may gradually lose the motivation toward the diet, especially in a latter portion of the diet period, thus making it difficult for the user to achieve the target activity amount TA. Therefore, updating the target activity amount TA on the basis of the actual activity amount AM during the diet period as in this embodiment encourages the user to maintain the motivation toward the diet so as to achieve the target.

The target activity calculation unit 50 calculates an estimated date of achievement of the target physical expenditure CS on the basis of the cumulative amount of the activity amount AM measured by the activity amount measurement unit 10 (step S68).

The step S70 to S74 in FIG. 3 are optional steps.

In this process, the activity monitor 100 accepts an input of weight information indicating the user's body weight (YES at step S70), and evaluates the achievement level AC with respect to the target energy intake TC at predetermined intervals, on the basis of the weight information and the activity amount AM actually measured. The weight information may be manually inputted by the user through the input unit 80, or the activity monitor 100 may include an interface unit (not shown) so as to receive measurement data from a scale.

Although the activity monitor 100 is capable of deciding whether the user's activity amount exceeds the target activity amount TA, by measuring the user's daily activity amount AM, the activity monitor 100 is unable to measure the amount of meal taken up by the user. Accordingly, the user's weight information may be employed as reference regarding whether the user is achieving the target energy intake. For example, in the case where, at a certain point in the diet period, the weight loss of the user is below the target despite the cumulative amount of the activity amount AM accomplishing the target activity amount TA, it can be presumed that the amount of meal exceeds the target energy intake TC. In this case, the difference between the inputted weight information and the weight at the time of target achievement (=initial weight−target physical expenditure CS) is adopted as an additional unachieved portion TR. The target activity calculation unit 50 recalculates the target activity amount TA and the target energy intake TC such that the additional unachieved portion TR is evenly achieved during the rest of the diet period, to thereby update the target activity amount TA (step S72). The activity monitor 100 outputs a message alerting the user that the energy intake is excessive (step S74).

Thereafter, the measurement of the activity amount AM is continued (step S50). Also in the case where the weight information has not been inputted at the step S70 (NO at step S70), the measurement of the activity amount AM is continued.

In contrast, in the case where it is decided that the target has been achieved or the measurement is finished (YES at step S62), a message to that effect is displayed on the output unit 90 (step S69).

The activity monitor 100 outputs risk information IR (step S69) alerting the user to weight regain that may follow a drastic diet, at the time of finishing the measurement upon achieving the target. The risk information IR may be outputted, for example, in the case where the target activity amount TA updated on the basis of the unachieved portion TR at the step S66 is greater than the target activity amount TA initially set at the step S40. This is because in such a case it can be presumed that the updated target activity amount TA constitutes a heavy burden on the user, which leads to higher risk of weight regain.

Thus, the activity monitor 100 calculates the unachieved portion TR of the target physical expenditure CS on the basis of the measurement result of the user's activity amount AM, and updates the target activity amount TA on the basis of the unachieved portion TR. Then the activity monitor 100 displays the risk information IR alerting the user to the risk of weight regain on the output unit 90, depending on the magnitude of the target activity amount TA at the time that the target physical expenditure CS has been achieved.

Second Embodiment

Figure 4:
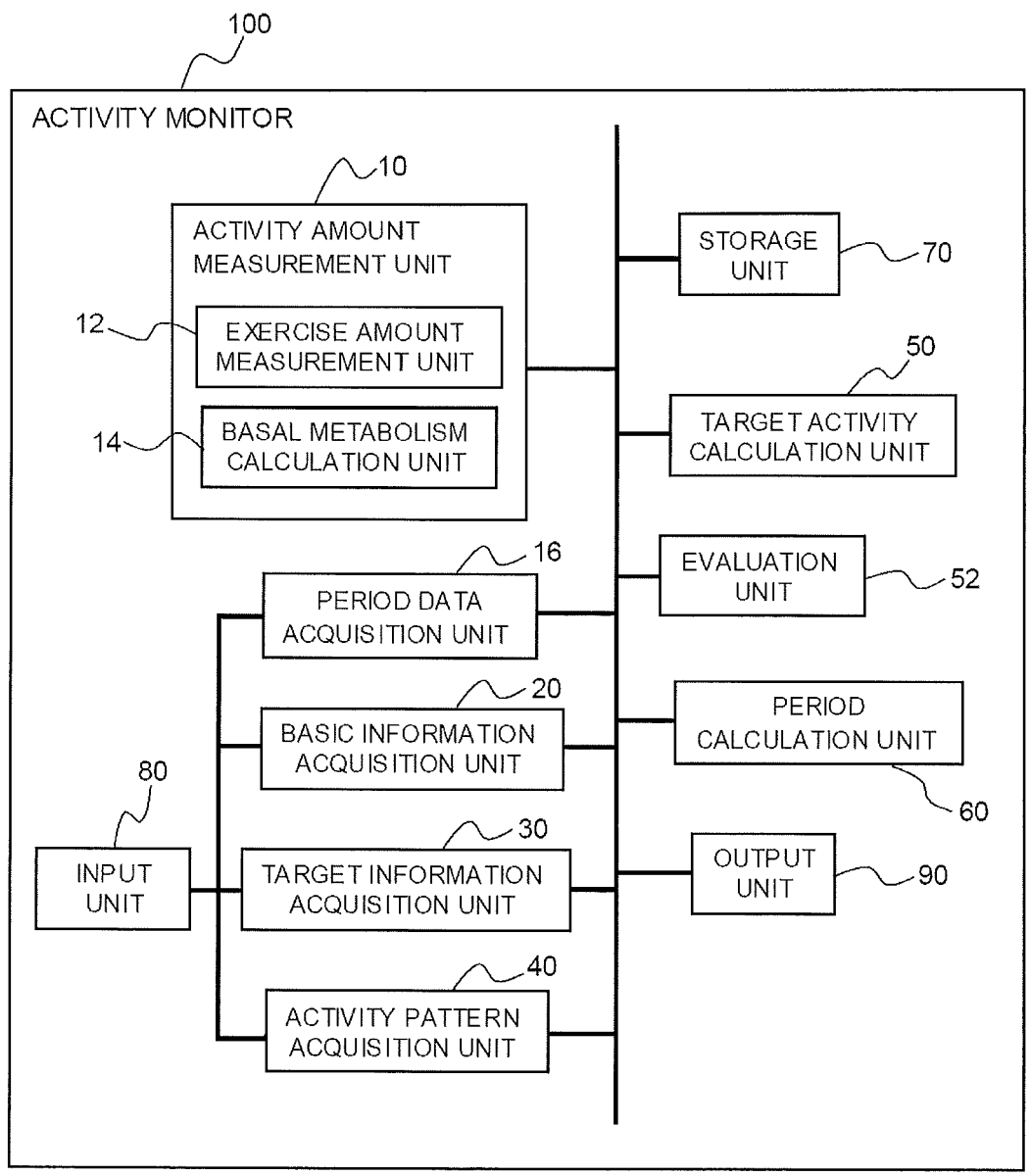
FIG. 4 is a functional block diagram of an activity monitor according to a second embodiment.
Figure 5:
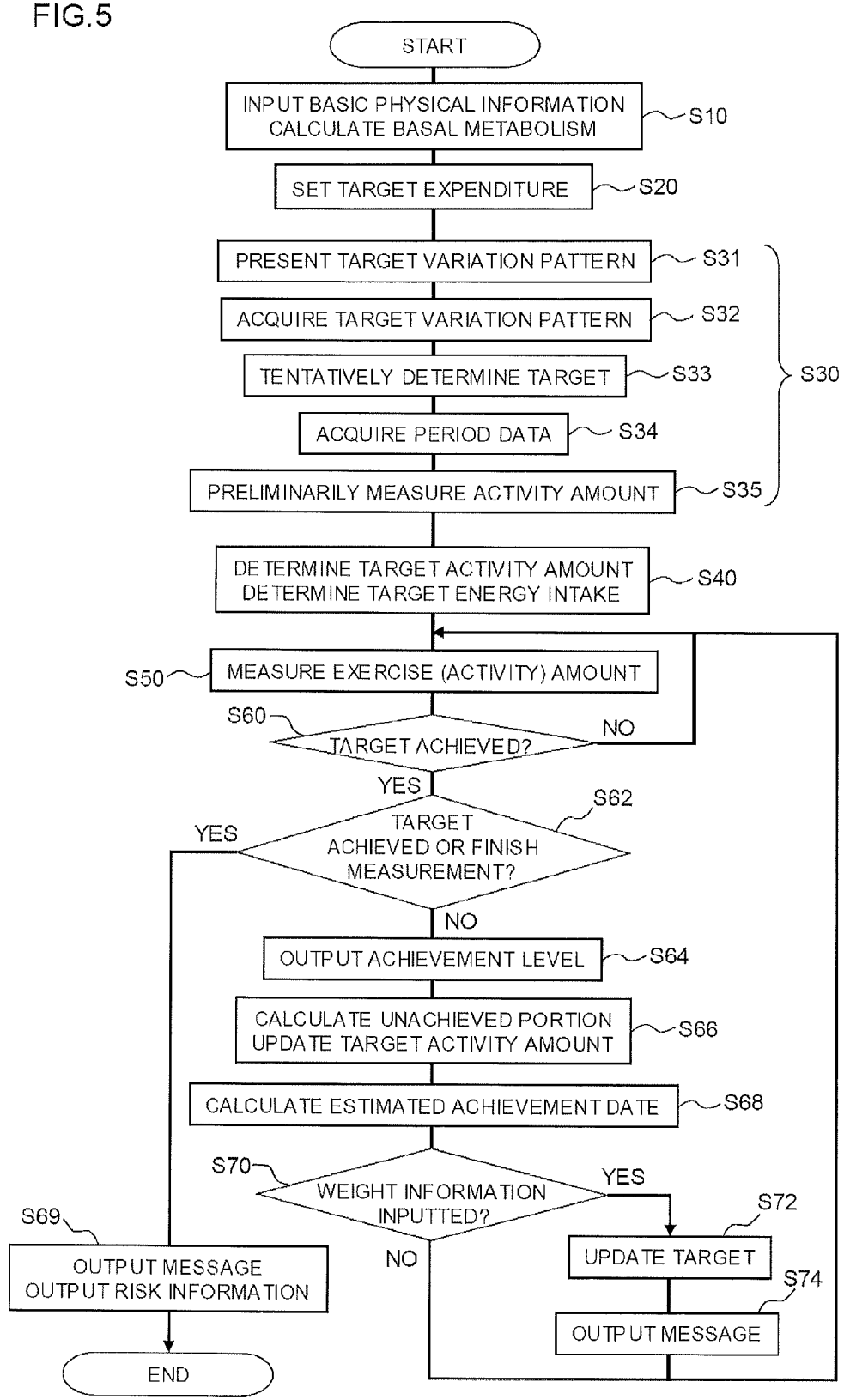
FIG. 5 is a flowchart showing a target activity amount calculation process according to the second embodiment.

FIG. 4 is a functional block diagram of the activity monitor 100 according to a second embodiment, and FIG. 5 is a flowchart showing a target activity amount calculation process performed utilizing the activity monitor 100 according to this embodiment.

The flowchart shown in FIG. 5 includes processes that may be selectively switched from the flowchart of the first embodiment shown in FIG. 3, by operating the input unit 80.

FIGS. 6A to 6D and 7A to 7C are diagrams showing a first to a seventh target variation patterns TP, respectively. The vertical axis of the diagrams represents the target fat loss Z per day (kcal/day). In the subsequent description, those points described referring to the first embodiment will not be repeated.

Figure 6A:
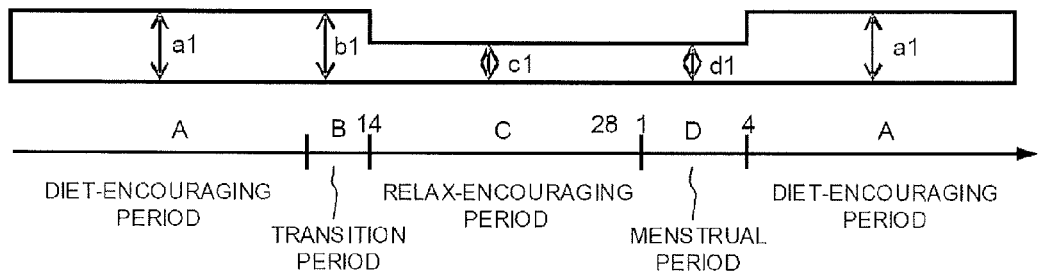
FIGS. 6A to 6D are diagrams showing a first to a fourth target variation patterns, respectively.

A menstrual cycle is broadly divided into a follicular phase from the first day of the menstrual period to ovulation, and a luteal phase from the ovulation to the first day of the next menstrual period. As schematically shown in FIG. 6A, generally the menstrual period D is approximately 4 days, the follicular phase A is approximately 8 days, the ovulation period B is approximately 4 days, and the luteal phase C is approximately 12 days, and hence the menstrual cycle is approximately 28 days. Information representing these periods is stored in the strage unit 70.

The luteal phase C is a high-temperature phase, during which the basal metabolism is greater than in the follicular phase A and hence higher exercise efficiency can be attained. During the luteal phase C, many women become mentally unstable and feel reluctant to actively exercise. The luteal phase C is further divided into a former half and a latter half, and in particular the latter approximately 6 days of the luteal phase immediately before the menstrual period D is called a premenstrual syndrome (PMS) period. Women suffering the PMS are prone to become physically and mentally unstable. Accordingly, in this embodiment a period corresponding to the follicular phase A will be denoted as diet-encouraging period, a period corresponding to the ovulation period B will be denoted as transition period, and a period corresponding to the luteal phase C will be denoted as relax-encouraging period.

A distinctive feature of the activity monitor 100 according to this embodiment is that the target activity amount TA and the target fat loss Z in a certain period of the menstrual cycle are set to be different from the target activity amount TA and the target fat loss Z in the remaining periods.

A first target variation pattern TP1 shown in FIG. 6A is arranged such that target fat loss a1, b1 for the follicular phase A and the ovulation period B are higher (a1=b1), and target fat loss c1, d1 for the luteal phase C and the menstrual period D are lower, but not zero (c1=d1).

Figure 6B:
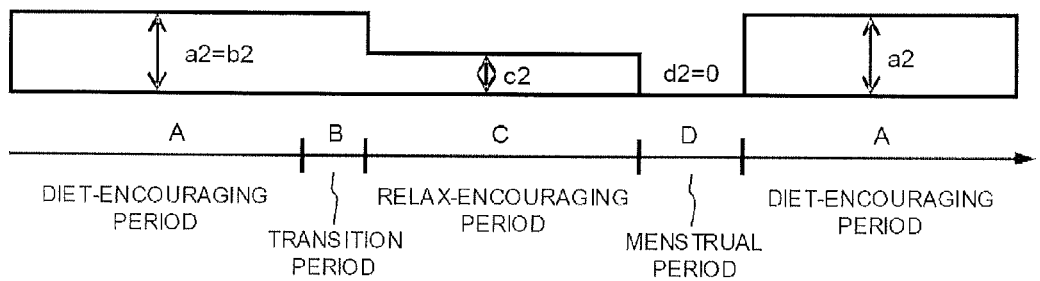

A second target variation pattern TP2 shown in FIG. 6B is arranged such that target fat loss a2, b2 for the follicular phase A and the ovulation period B are higher (a2=b2), while target fat loss c2 for the luteal phase C is lower and target fat loss d2 for the menstrual period D is zero.

Figure 6C:
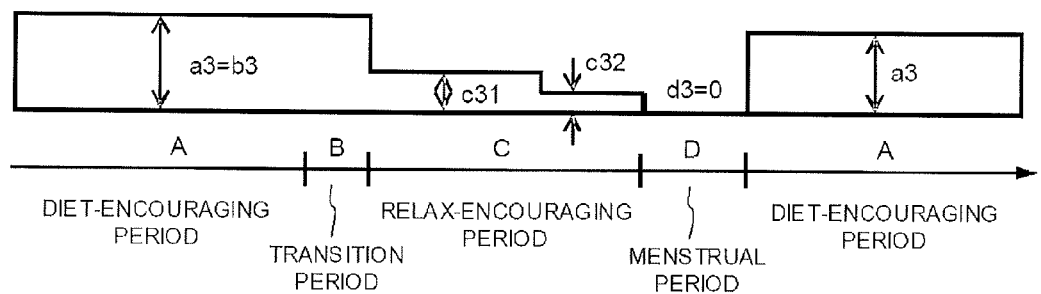

A third target variation pattern TP3 shown in FIG. 6C is arranged such that target fat loss a3, b3 for the follicular phase A and the ovulation period B are higher (a3=b3), while target fat loss c31 for the former half of the luteal phase C is lower, target fat loss c32 for the latter half of the luteal phase C is even lower, and target fat loss d3 for the menstrual period D is zero.

Figure 6D:
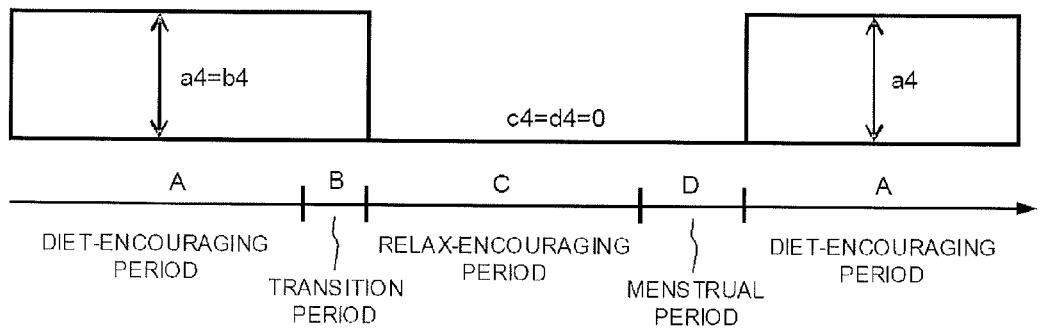

A fourth target variation pattern TP4 shown in FIG. 6D is arranged such that the diet is performed only for the follicular phase A and the ovulation period B so as to achieve target fat loss a4, b4 (a4=b4), and target fat loss c4, d4 for the luteal phase C and the menstrual period D are both zero.

Figure 7A:
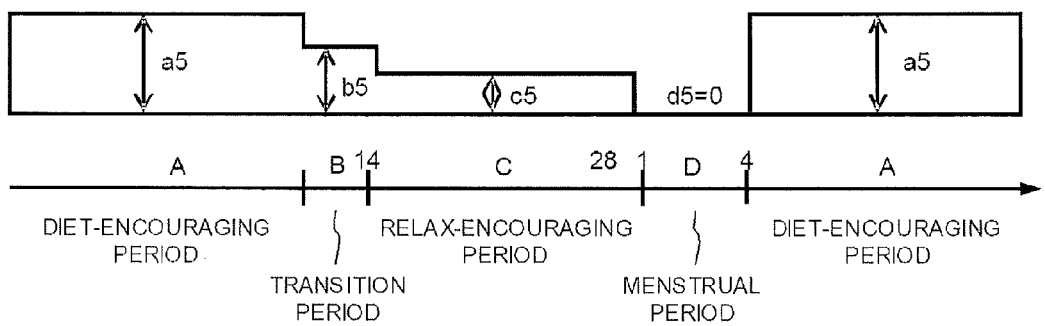
FIGS. 7A to 7C are diagrams showing a fifth to a seventh target variation patterns, respectively.

A fifth target variation pattern TP5 shown in FIG. 7A is different from the second target variation pattern TP2 shown in FIG. 6B in that target fat loss b5 for the ovulation period B is an intermediate value between target fat loss a5 for the follicular phase A and target fat loss c5 for the luteal phase C.

Figure 7B:
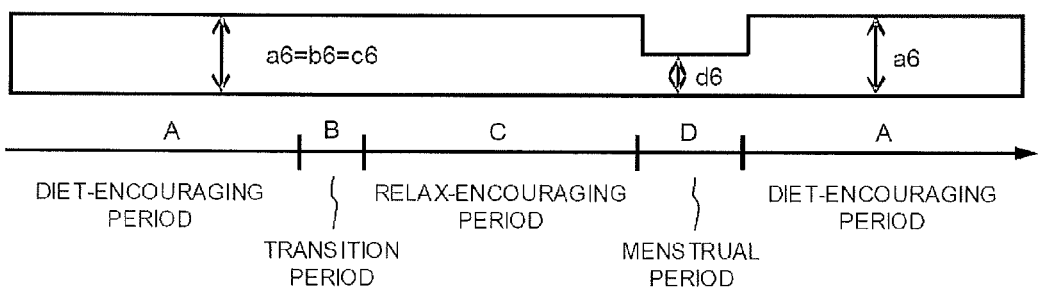

A sixth target variation pattern TP6 shown in FIG. 7B is different from the first target variation pattern TP1 shown in FIG. 6A in that target fat loss c6 for the luteal phase C is the same as target fat loss a6, b6 for the follicular phase A and the ovulation period B.

Figure 7C:
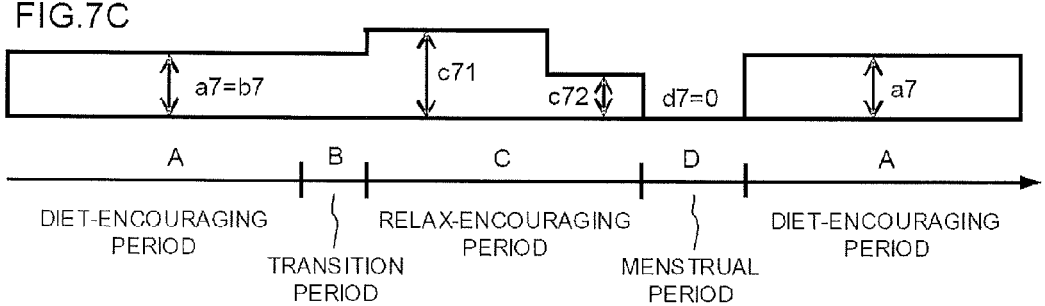

A seventh target variation pattern TP7 shown in FIG. 7C is different from the third target variation pattern TP3 shown in FIG. 6C in that target fat loss c71 for the former half of the luteal phase C is higher than target fat loss a7, b7 (a7=b7) for the follicular phase A and the ovulation period B.

The activity monitor 100 according to this embodiment presents target images showing different levels of target fat loss for each phase in the menstrual cycle, as exemplified by the target variation patterns TP1 to TP7 (step S31 in FIG. 5), so that the user can selected a desired target image (step S32).

More specifically, the activity pattern acquisition unit 40 according to this embodiment indicates the target variation patterns TP1 to TP7, each specifying different tendencies of the target activity amount TA for each phase in the menstrual cycle, and acquires the target variation pattern TP selected by the user, as the pattern information.

Therefore, the target activity amount TA can be meticulously specified in accordance with the target variation pattern TP that represents the user's desire.

Hereunder, description of this embodiment will be made on the assumption that the target variation pattern TP3 shown in FIG. 6C is selected.

As in the first embodiment, the basic information acquisition unit 20 acquires the basic physical information BA inputted through the input unit 80. The target information acquisition unit 30 acquires the target physical expenditure CS inputted through the input unit 80. Then the activity pattern acquisition unit 40 accepts the physical activity level (PAL, see equation (2)) and the distribution ratio, through the input unit 80.

The target activity calculation unit 50 calculates the basal metabolism and the standard activity amount, and then calculates the target activity amount TA and the target energy intake TC in accordance with the foregoing equations (4) and (5). In this embodiment, however, since the diet is not to be performed during the menstrual period D, the following equation (3a) is adopted instead of the equation (3), to obtain the target fat loss Z.

[Equation 6]

$$\text{Target fat loss } Z \text{ per day(kcal/day)}=3 \text{ kgs}/(90 \text{ days}-4 \text{ days}\times 3)\times 7200(\text{kcal/kg})=277(\text{kcal/day}) \quad (3a)$$

The distribution ratio in this embodiment is 7:3, 7 representing the decrease in energy intake and 3 representing the increase in energy expenditure by exercise, as in the first embodiment. Accordingly, the target decrease in energy intake can be set as 194 kcal/day ($Z\times 0.7$), and the target increase in energy expenditure by exercise can be set as 83 kcal/day ($Z\times 0.3$). Thus the target activity amount TA can be obtained as 1982 kcal/day (1899+83) in accordance with the equation (4). Likewise, the target energy intake TC can be obtained as 1705 kcal/day (1899-194) in accordance with the equation (5).

The target activity calculation unit 50 then determines the target fat loss a3, b3, c31, c32 in accordance with the target variation pattern TP3.

The target activity calculation unit 50 according to this embodiment calculates the target activity amount TA for the follicular phase A so as to be higher than the target activity amount TA for the menstrual period D and the luteal phase C.

Generally, it is preferable to refrain from exercising and relax during the menstrual period D. The luteal phase C is a high-temperature phase during which the basal metabolism increases, but on the other hand the user is prone to become mentally instable, and therefore it is preferable to set the target activity amount TA per day at a lower level to facilitate the user to achieve the target. In contrast, the follicular phase A is a period during which both physical and mental conditions are stabilized, and hence most suitable for actively exercising and restricting energy intake. Accordingly, the follicular phase A is a good opportunity to set a higher target activity amount TA so as to achieve significant energy expenditure that would make up lower performance during another phase. Thus, the activity monitor 100 according to this embodiment calculates at least one target pattern in which the target activity amount TA for the follicular phase A is set higher than the target for the menstrual period D and the luteal phase C. In this embodiment, the first to the fifth target variation patterns TP1 to TP5 correspond to this case.

The target activity calculation unit 50 calculates the target energy intake TC for the follicular phase A so as to be lower than the target energy intake TC for the luteal phase C.

During the PMS period in the latter half of the luteal phase the user often suffers physical and mental disorder, and hence it is preferable to loosen the restriction of energy intake. In this case, it is preferable to set lower target energy intake TC for the follicular phase A, to thereby allow the user to take up sufficient energy during the luteal phase C. Such an arrangement allows the diet target for the luteal phase C to be set at a mild level without compromising the progress of the diet. For the same reason, the luteal phase C may be divided into the former half and the latter half, and the target energy intake TC for the former half may be calculated so as to be lower than the target energy intake TC for the latter half (PMS period). More specifically, the energy intake for the follicular phase A may be reduced by 5 to 15% from the energy intake during the menstrual period D.

Further detail will be described here below. Studies accomplished by the present inventors show that the basal metabolism during the follicular phase A drops by approximately 9% in comparison with the basal metabolism during the luteal phase C, and that hence the energy intake may be reduced in the corresponding amount. In this embodiment, accordingly, the energy intake (=68 kcal) corresponding to the distribution ratio (0.7) with respect to 9% (98 kcal) of the basal metabolism (1085 kcal/day) is reduced during the follicular phase A (8 days) and the ovulation period B (4 days), totally for 12 days, and this amount is equally divided for the PMS period in the latter half of the luteal phase C (6 days) so as to mitigate the target energy intake TC. Likewise, regarding the target increase in energy expenditure by exercise also, the energy expenditure by exercise (=29 kcal) corresponding to the distribution ratio (0.3) with respect to 9% (98 kcal) of the basal metabolism (1085 kcal/day) is added during the follicular phase A (8 days) and the ovulation period B (4 days), totally for 12 days, so as to achieve higher progress of the diet, and this amount is equally divided for the PMS period in the latter half of the luteal phase C (6 days) so as to mitigate the target activity amount TA.

Thus, the activity monitor 100 according to this embodiment reserves a part of the target energy intake TC and increases the target activity amount TA during the follicular phase A and the ovulation period B which are suitable for diet, and allocates those amounts to the target energy intake TC and the target activity amount TA for the PMS period so as to mitigate the target. Such an arrangement exempts the user from suffering excessive restriction of energy intake during the PMS period which makes the user mentally unstable, thereby facilitating the user to achieve the diet target.

As stated earlier, the activity pattern acquisition unit 40 according to this embodiment acquires, as the pattern information, the information indicating the distribution ratio between the target decrease in energy intake and the target increase in energy expenditure by exercise, and the allocation information indicating the arrangement of the target activity amount TA for the luteal phase C and the follicular phase A. Then the target activity calculation unit 50 calculates the target activity amount TA with different distribution ratios for the luteal phase C and the follicular phase A.

The allocation information indicates differences in target activity amount TA between the luteal phase C and the follicular phase A. In other words, the activity monitor 100 according to this embodiment determines the target variation pattern TP on the basis of both the distribution ratio indicating the ratio of restriction of energy intake to the increase in exercise amount and the allocation information indicating the difficulty level of the diet target of each phase in the menstrual cycle.

In general, the energy expenditure by exercise and the energy intake that a female user can achieve without an excessive effort fluctuate in each phase in the menstrual cycle, and the amplitude of such fluctuation largely differs user by user. Accordingly, taking into account both the distribution ratio and the allocation information as in this embodiment allows the diet target for female users to be meticulously determined.

It is to be noted that, after a period data acquisition unit 16 (to be subsequently described) acquires period data DT so as to accurately recognize the user's menstrual cycle, the reserved amount of the target energy intake TC and the added amount of the target activity amount TA may be calculated on the basis of the total days corresponding to the user's own period of the follicular phase A and the ovulation period B. Through the foregoing process, the target value (target energy intake TC and target activity amount TA) from the follicular phase A to the menstrual period D can be tentatively determined (step S33 in FIG. 5).

The activity monitor 100 according to this embodiment shown in FIG. 4 is different from that of the first embodiment in including the period data acquisition unit 16 and a period calculation unit 60.

The period data acquisition unit 16 acquires period data DT indicating the period in the menstrual cycle (step S34). As will be subsequently described, the target activity calculation unit 50 according to this embodiment determines different target activity amounts TA for each phase in the menstrual cycle, on the basis of the basic physical information BA, the target physical expenditure CS, the pattern information, and the period data DT.

The period data acquisition unit 16 accepts an input of reference date information RD indicating the first day of the menstrual period, as the period data DT. The activity monitor 100 then calculates the period in the menstrual cycle on the basis of the reference date information RD and the number of elapsed days after the acceptance of the period data DT.

The activity monitor 100 includes the period calculation unit 60 having a timer counter (not shown) and the output unit 90 that displays text information such as numerals and messages. The period calculation unit 60 counts the elapsed time from the start of the measurement of the user's activity amount AM. Such a configuration allows the expiration of the diet period and the transition of the user's menstrual cycle to be monitored.

The output unit 90 serves to display a measurement result of the activity amount AM. More specifically, the output unit 90 includes one or more display devices and a display controller. The output unit 90 according to this embodiment includes a period data display unit 92 (see FIG. 1). The period data display unit 92 displays the current phase of the female user's menstrual cycle by a text, a mark, a symbol, or a combination thereof, on the basis of the period data DT acquired by the period data acquisition unit 16. The period data display unit 92 according to this embodiment occupies a section therefor in a part of the display device of the output unit 90.

The period data display unit 92 displays a period name (for example, diet-encouraging period) indicating that the current period is suitable for diet, in the case where the period in the menstrual cycle represented by the period data DT corresponds to the follicular phase A. In the case where the period data DT represents a period corresponding to the luteal phase C, the period data display unit 92 displays another period name (for example, relax-encouraging period) indicating that it is preferable to set a milder diet target than in the follicular phase. In the case where the period data DT represents a period corresponding to the ovulation period, the period data display unit 92 displays still another period name (for example, transition period) indicating that it is preferable to set a milder diet target than in the follicular phase, because the user's physical condition is prone to fluctuate although the period is suitable for diet. The period data display unit 92 thus announces the current period in the menstrual cycle to the female user.

Alternatively, the period data display unit 92 may display a text message corresponding to the diet-encouraging period or relax-encouraging period. For example, a message that rouses the user to make exercise such as "Keep it up!" may be displayed in the diet-encouraging period. In the relax-encouraging period, a message that can alleviate the user's mental burden such as "Take it easy" would be appropriate. The period data display unit 92 may display an icon representing the phase in the menstrual cycle. For example, a heart symbol (see FIG. 1) may be displayed in the menstrual period.

Although the reference date information RD can be typically exemplified by the elapsed days from the first day of the menstrual period (inclusive of the first day), the period calculation unit 60 may accept a basal body temperature measured by the user, to thereby decide which of the menstrual period D, the luteal phase C, or the follicular phase A the user is in. The period data acquisition unit 16 may acquire such a decision result as the period data DT.

Thus, the activity monitor 100 according to this embodiment calculates the target activity amount TA in consideration of the phase in the female user's menstrual cycle. Calculating thus the target activity amount TA on the basis of the pattern information indicating the arrangement of the activity amount AM, as well as the period data DT regarding the fluctuation of the user's basal metabolism and exercise efficiency, allows a moderate diet target that fits the user's life style to be presented.

In addition, the activity monitor 100 according to this embodiment allows the user to recognize the start or end of the diet-encouraging period (follicular phase A and ovulation period B), the start or end of the relax-encouraging period (luteal phase C), and the first day of the next menstrual period, to thereby facilitate the user to make up the activity plan.

The period data acquisition unit 16 may accept the input of the reference date information by the user each time the first day of the menstrual period comes. This allows the user's menstrual cycle to be accurately recognized. The period data DT can be inputted by operating the input unit 80.

A feature of the activity pattern acquisition unit 40 according to this embodiment is that it acquires the pattern information on the basis of the activity amount measured by the activity amount measurement unit 10. More specifically, the activity pattern acquisition unit 40 calculates or chooses the pattern information on the basis of the activity amount. Such an arrangement allows the target activity amount TA to be calculated on the basis of the user's actual activity pattern. Therefore, the activity monitor 100 according to this embodiment can calculate the target activity amount TA that fits the user's life style, and a moderate diet target can be presented. For this purpose, the activity monitor 100 according to this embodiment monitors the user's activity pattern in advance with the activity amount measurement unit 10 that measures the user's activity amount AM to thereby estimate the energy expenditure, and decides the target variation pattern TP suitable for the user with the target activity calculation unit 50.

The target activity calculation unit 50 according to this embodiment measures the user's activity amount (preliminary measurement result AM0) during a predetermined preliminary measurement period before the diet (step S35 in FIG. 5), and calculates the target activity amount TA on the basis of the preliminary measurement result AM0 thus measured. The preliminary measurement period may be set from a few days to a week. The user is requested to spend the preliminary measurement period in a life style as natural as possible. Such an arrangement allows a natural balance level between the total energy expenditure and the energy intake of the user to be recognized. For female users, it is preferable to acquire the pattern information in consideration of which phase of the menstrual cycle the preliminary measurement period corresponds to.

The foregoing process allows the user to perform the diet without distinction between the preliminary measurement period and the subsequent measurement period of the activity amount. More specifically, at the step S35 the achievement level AC is evaluated on the basis of the difference between the activity amount (preliminary measurement result AM0) measured by the activity amount measurement unit 10 and the target activity amount TA tentatively determined at the step S33, and the corresponding target fat loss Z is subtracted from the target physical expenditure CS. Such an arrangement allows the achievement level of the target physical expenditure CS inclusive of the diet result during the preliminary measurement period to be evaluated, without incurring a disadvantage in that the diet cannot be started during the preliminary measurement period.

The activity amount measurement unit 10 includes the exercise amount measurement unit 12 that measures the user's exercise amount and the basal metabolism calculation unit 14 that calculates the user's basal metabolism on the basis of the basic physical information BA. The activity pattern acquisition unit 40 acquires the exercise amount actually measured by the exercise amount measurement unit 12 as the pattern information. Through such a process, the ordinary basal metabolism and exercise amount of the user before the diet can be obtained. The total of the basal metabolism and the exercise amount can be presumed to be equivalent to the calorie intake that stabilizes the user's body weight, in other words the balance level between the user's expenditure and intake can be recognized.

The activity pattern acquisition unit 40 accepts the input of the pattern information by the user. Then the diet target that fits the activity pattern desired by the user is set. The activity monitor 100 displays a questionnaire for classifying the user's activity pattern into a plurality of patterns, and accepts an input responding the questionnaire as the pattern information.

The activity pattern acquisition unit 40 acquires the pattern information on the basis of the activity amount AM measured by the activity amount measurement unit 10 in association with the period data DT. The activity pattern acquisition unit 40 associates, in particular, the information on whether the user is in the luteal phase C, the menstrual period D, or the follicular phase A, with the activity amount AM, when acquiring the pattern information.

Accordingly, the activity pattern acquisition unit 40 can acquire the pattern information reflecting the information indicating which phase of the menstrual cycle the activity amount (preliminary measurement result AM0) measured in the preliminary measurement period corresponds to, and therefore the diet target suitable for the user can be meticulously determined. More specifically, the distribution ratio of the energy expenditure by exercise for the luteal phase C and the follicular phase A can be automatically determined on the basis of the actual activity amount (preliminary measurement result AM0) measured in the preliminary measurement period. At a certain level of the preliminary measurement result AM0, in the case where the preliminary measurement period corresponds to the menstrual period D or the luteal phase C, i.e., the period that discourages the user from exercising, the user can be presumed to be of a type who is relatively active in exercising. This is because the user is performing a certain amount of activity despite the period discouraging the user from exercising. Conversely, in the case where the preliminary measurement period corresponds to the follicular phase A, i.e., the period that encourages the user to exercise, the user can be presumed to be of a type who is relatively inactive in exercising.

Accordingly, the activity monitor 100 according to this embodiment may acquire as the pattern information a value obtained by multiplying the preliminary measurement result AM0 measured in the preliminary measurement period by a coefficient smaller than 1, in the case where the period indicated by the period data DT corresponds to the follicular phase A. In the case where the period indicated by the period data DT corresponds to the menstrual period D or the luteal phase C, the activity monitor 100 may acquire as the pattern information a value obtained by multiplying the preliminary measurement result AM0 measured in the preliminary measurement period by a coefficient greater than 1. Such an arrangement allows the target activity calculation unit 50 to determine the target variation pattern TP that fits the user's activity pattern, without the input of the distribution ratio by the user. The target activity amount TA and the target energy intake TC can thus be determined (step S40 in FIG. 5).

In this embodiment, the user's activity amount may be preliminarily measured for a predetermined period so as to acquire the pattern information, and an additional expenditure by exercise AA may be added to the preliminarily measured activity amount (preliminary measurement result AM0) to thereby calculate the target activity amount TA. The additional expenditure by exercise AA is, for example, a value obtained by multiplying the amount of the equation (3a) by the distribution ratio of the target increase in energy expenditure by exercise.

Regarding the evaluation of the achievement level AC, the activity monitor 100 according to this embodiment is the same as that of the first embodiment in including the evaluation unit 52 that compares the calculated target activity amount TA and the activity amount AM measured by the activity amount measurement unit 10 to thereby evaluate the achievement level AC. However, activity monitor 100 according to this embodiment is different from that of the first embodiment in that the former outputs the evaluation result in different manners in the luteal phase C and the follicular phase A, when the evaluated achievement level AC is the same.

During the luteal phase C, especially in the PMS period in the latter half of the luteal phase the user often becomes mentally unstable, and hence sometimes it may be preferable to present a lenient evaluation even though the diet target has not been achieved, in order to prevent the user from losing the motivation toward the diet. Conversely, in the follicular phase A where the user is mentally stable, it may be preferable to present a severe evaluation so as to rouse the user to try harder. Therefore, the activity monitor 100 according to this embodiment outputs the evaluation result in different manners in the luteal phase C and the follicular phase A, in response to generally the same extent of unfulfillment of the target. Such an arrangement allows the user to maintain the motivation, thereby leading the user to successful achievement of the diet target. The remaining portions of the process are the same as those of the first embodiment, and hence the description will not be repeated.

The present invention is in no way limited to the foregoing embodiments, but includes various modifications and improvements as far as an object of the present invention is achieved.

The first and the second embodiment encompasses the following technical idea.

(1) An activity monitor having an activity amount measurement unit that measures an activity amount of a user, including a basic information acquisition unit that accepts an input of basic physical information on the user's body, a target information acquisition unit that accepts an input of a target physical expenditure of the user, an activity pattern acquisition unit that acquires pattern information indicating the user's intent on the activity amount, and a target activity calculation unit that determines a target activity amount on the basis of the basic physical information, the target physical expenditure, and the pattern information acquired by the activity pattern acquisition unit.

(2) The activity monitor according to (1) above, wherein the activity pattern acquisition unit acquires the pattern information on the basis of the activity amount measured by the activity amount measurement unit.

(3) The activity monitor according to (2) above, wherein the activity amount measurement unit includes an exercise amount measurement unit that measures the user's exercise amount, and a basal metabolism calculation unit that calculates the user's basal metabolism on the basis of the basic physical information, and the activity pattern acquisition unit acquires the exercise amount measured by the exercise amount measurement unit as the pattern information.

(4) The activity monitor according to any one of (1) to (3) above, wherein the activity pattern acquisition unit acquires distribution information indicating a distribution ratio of a decrease in energy intake to an increase in energy expenditure by exercise as the pattern information, and the target activity calculation unit determines target energy intake and the target activity amount on the basis of the distribution information and the target physical expenditure.

(5) The activity monitor according to any one of (1) to (4) above, wherein the activity pattern acquisition unit accepts an input of the pattern information by the user.

(6) The activity monitor according to any one of (1) to (5) above, further including a period data acquisition unit that acquires period data indicating a period in a menstrual cycle, wherein the target activity calculation unit determines the target activity amounts that are different for each period in the menstrual cycle, on the basis of the basic physical information, the target physical expenditure, the pattern information, and the period data.

(7) The activity monitor according to (6) above, further including an output unit that outputs a period name indicating that the period in the menstrual cycle is suitable for diet in the case where the period corresponds to a follicular phase, and outputs another period name indicating that it is preferable to set a milder diet target than in the follicular phase in the case where the period corresponding to a luteal phase, to thereby notify the user of the period.

(8) The activity monitor according to (6) or (7) above, wherein the activity pattern acquisition unit presents a plurality of target variation patterns each representing the target activity amounts arranged in different manners for each period in the menstrual cycle, and acquires a selected one of the target variation pattern as the pattern information.

(9) The activity monitor according to any one of (6) to (8) above, wherein the target activity calculation unit determines the target activity amount for the follicular phase at a higher level than the target activity amount for a menstrual period and the luteal phase.

(10) The activity monitor according to any one of (6) to (9) above, wherein the activity pattern acquisition unit acquires the pattern information on the basis of the activity amount measured by the activity amount measurement unit in association with the period data.

(11) The activity monitor according to any one of (6) to (10) above, wherein the activity pattern acquisition unit acquires, as the pattern information, distribution information indicating a distribution ratio between a decrease in energy intake and an increase in energy expenditure by exercise, and allocation information indicating an arrangement of the target activity amount for the luteal phase and the follicular phase, and the target activity calculation unit determines the target activity amount with the distribution ratios that are different for the luteal phase and the follicular phase.

(12) The activity monitor according to any one of (6) to (11) above, wherein the target activity calculation unit determines a target energy intake for the follicular phase at a lower level than a target energy intake for the luteal phase.

(13) The activity monitor according to any one of (6) to (12) above, wherein the period data acquisition unit accepts an input of reference date information indicating a first day of the menstrual period as the period data, and calculates the period in the menstrual cycle on the basis of the reference date information and the number of elapsed days after the acceptance of the period data.

(14) The activity monitor according to any one of (1) to (13) above, further including an evaluation unit that evaluates an achievement level through comparison of the target activity amount determined and the activity amount measured by the activity amount measurement unit.

(15) The activity monitor according to any one of (6) to (13) above, further including an evaluation unit that evaluates an achievement level through comparison of the target activity amount determined and the activity amount measured by the activity amount measurement unit, wherein the activity monitor being configured to output an evaluation result in different manners for the luteal phase and the follicular phase, when the evaluated achievement level is the same.

(16) The activity monitor according to (14) or (15) above, wherein the target activity calculation unit calculates an unachieved portion of the target physical expenditure on the basis of a cumulative amount of the activity amounts measured by the activity amount measurement unit, and updates the target activity amount on the basis of the unachieved portion.

(17) The activity monitor according to any one of (1) to (16) above, wherein the target activity calculation unit calculates an estimated date of achievement of the target physical expenditure on the basis of the cumulative amount of the activity amount measured by the activity amount measurement unit.

(18) A method of calculating a target activity amount, including accepting an input of basic physical information on a user's body, accepting an input of a target physical expenditure of the user, acquiring pattern information indicating the user's intent on the activity amount, and determining the target activity amount on the basis of the basic physical information, the target physical expenditure, and the pattern information acquired by the activity pattern acquisition unit.

(19) The method according to (18) above, further including preliminarily measuring the user's activity amount for a predetermined period thereby acquiring the pattern information, and adding an additional expenditure by exercise to the activity amount preliminarily measured, thereby determining the target activity amount.

(20) The method according to (18) or (19) above, further including measuring the user's activity amount, and evaluating an achievement level with respect to the target activity amount at predetermined intervals on the basis of the activity amount measured and the target activity amount.

(21) The method according to any one of (18) to (20) above, further including accepting an input of weight information indicating the user's body weight, and evaluating an achievement level with respect to a target energy intake at predetermined intervals on the basis of the weight information and the activity amount measured.

(22) The method according to any one of (18) to (21) above, further including calculating an unachieved portion of the target physical expenditure on the basis of a measurement result of the user's activity amount thereby updating the target activity amount on the basis of the unachieved portion, and outputting risk information alerting the user to a risk of weight regain, depending on a magnitude of the target activity amount at the time that the target physical expenditure has been achieved.

(23) A storage medium containing a program for causing an activity monitor having an activity amount measurement unit to execute a calculation of a target activity amount, wherein the calculation of a target activity amount includes accepting an input of basic physical information on a user's body, accepting an input of a target physical expenditure of the user, acquiring pattern information indicating the user's intent on the activity amount, and determining the target activity amount on the basis of the basic physical information, the target physical expenditure, and the pattern information acquired by the activity pattern acquisition unit.

It is apparent that the present invention is not limited to the above embodiment, and may be modified and changed without departing from the scope and spirit of the invention.

What is claimed is:

1. An activity monitor having an activity amount measurement unit that measures an activity amount of a user, comprising:
    a basic information acquisition unit that accepts an input of basic physical information on the user's body;
    a target information acquisition unit that accepts an input of a target physical expenditure of the user;
    an activity pattern acquisition unit that acquires an allocation information indicating a difficulty level of a diet target of each of prescribed periods:
    a target activity calculation unit that determines, in each of the prescribed periods which are included in a diet period of the user, target activity amounts expressed as numerical quantities which correspond to the difficulty level of the diet target of each of the prescribed periods on the basis of the basic physical information, the target physical expenditure, and the allocation information: and
    a period data acquisition unit that acquires period data indicating a period in a menstrual cycle,
    wherein the target activity calculation unit determines the target activity amounts that are different for each period in the menstrual cycle, on the basis of the basic physical information, the target physical expenditure, the allocation information, and the period data.

2. The activity monitor according to claim 1,
    wherein the activity pattern acquisition unit acquires pattern information on the basis of the activity amount measured by the activity amount measurement unit.

3. The activity monitor according to claim 2,
    wherein the activity amount measurement unit comprises an exercise amount measurement unit that measures the user's exercise amount, and a basal metabolism calculation unit that calculates the user's basal metabolism on the basis of the basic physical information, and
    the activity pattern acquisition unit acquires the exercise amount measured by the exercise amount measurement unit as the pattern information.

4. The activity monitor according to claim 1,
    wherein the activity pattern acquisition unit acquires distribution information indicating a distribution ratio of a decrease in energy intake to an increase in energy expenditure by exercise as the pattern information, and
    the target activity calculation unit determines target energy intake and the target activity amount on the basis of the distribution information and the target physical expenditure.

5. The activity monitor according to claim 1,
    wherein the activity pattern acquisition unit accepts an input of the allocation information by the user.

6. The activity monitor according to claim 1, further comprising an output unit that outputs a period name indicating that the period in the menstrual cycle is suitable for diet in the case where the period corresponds to a follicular phase, and outputs another period name indicating that it is preferable to set a milder diet target than in the follicular phase in the case where the period corresponds to a luteal phase, to thereby notify the user of the period.

7. The activity monitor according to claim 1,
    wherein the activity pattern acquisition unit presents a plurality of target variation patterns each representing the target activity amounts arranged in different manners for each period in the menstrual cycle, and acquires a selected one of the target variation patterns as the allocation information.

8. The activity monitor according to claim 1,
    wherein the target activity calculation unit determines the target activity amount for the follicular phase at a higher level than the target activity amount for a menstrual period and the luteal phase.

9. The activity monitor according to claim 1,
    wherein the activity pattern acquisition unit acquires pattern information on the basis of the activity amount measured by the activity amount measurement unit in association with the period data.

10. The activity monitor according to claim 1,
    wherein the activity pattern acquisition unit acquires, as pattern information, distribution information indicating a distribution ratio between a decrease in energy intake and an increase in energy expenditure by exercise, and allocation information indicating an arrangement of the target activity amount for the luteal phase and the follicular phase,
    and the target activity calculation unit determines the target activity amount with the distribution ratios that are different for the luteal phase and the follicular phase.

11. The activity monitor according to claim 1,
    wherein the target activity calculation unit determines a target energy intake for the follicular phase at a lower level than a target energy intake for the luteal phase.

12. The activity monitor according to claim 1,
    wherein the period data acquisition unit accepts an input of reference date information indicating a first day of the menstrual period as the period data, and calculates the period in the menstrual cycle on the basis of the reference date information and the number of elapsed days after the acceptance of the period data.

13. The activity monitor according to claim 1, further comprising an evaluation unit that evaluates an achievement level through comparison of the target activity amount determined and the activity amount measured by the activity amount measurement unit.

14. The activity monitor according to claim 1, further comprising an evaluation unit that evaluates an achievement level through comparison of the target activity amount determined and the activity amount measured by the activity amount measurement unit,
    wherein the activity monitor being configured to output an evaluation result in different manners for the luteal phase and the follicular phase, when the evaluated achievement level is the same.

15. The activity monitor according to claim 13,
    wherein the target activity calculation unit calculates an unachieved portion of the target physical expenditure on the basis of a cumulative amount of the activity amounts measured by the activity amount measurement unit, and updates the target activity amount on the basis of the unachieved portion.

16. The activity monitor according to claim 1, wherein the target activity calculation unit calculates an estimated date of achievement of the target physical expenditure on the basis of the cumulative amount of the activity amount measured by the activity amount measurement unit.

* * * * *